United States Patent [19]

Gold

[11] Patent Number: 4,463,765
[45] Date of Patent: Aug. 7, 1984

[54] SCREW-IN PACING LEAD ASSEMBLY
[75] Inventor: Philip Gold, Pompano Beach, Fla.
[73] Assignee: Cordis Corporation, Miami, Fla.
[21] Appl. No.: 412,425
[22] Filed: Aug. 30, 1982
[51] Int. Cl.³ .............................................. A61N 1/04
[52] U.S. Cl. ................................... 128/785; 128/419 P
[58] Field of Search ......................... 128/642, 784-786, 128/419 P

[56] References Cited

U.S. PATENT DOCUMENTS

| 4,106,512 | 8/1978 | Bisping .................................. 128/785 |
| 4,217,913 | 8/1980 | Dutcher ................................. 128/785 |
| 4,311,153 | 1/1982 | Smits .................................... 128/785 |
| 4,381,013 | 4/1983 | Dutcher ................................. 128/786 |
| 4,402,330 | 9/1983 | Lindemans ............................. 128/786 |

FOREIGN PATENT DOCUMENTS 2806069 8/1979 Fed. Rep. of Germany ...... 128/785

Primary Examiner—Lee S. Cohen
Attorney, Agent, or Firm—Henry W. Collins; Thomas R. Vigil

[57] ABSTRACT

The screw-in lead assembly can be connected at its proximal end to an electrical power source and can be connected at its distal end to tissue of a living body. The assembly comprises at least one wire conductor extending within a sheath of material inert to body materials. A proximal end of the wire conductor can be electrically connected to the power source and a distal end of the wire conductor can be electrically connected to a tubular electrode body in an electrode assembly at the distal end of the lead. A corkscrew shaped securing device is received within the tubular body and has a proximal end fixed to a movable mounting member in the tubular body. A drive mechanism in the form of a helical metal ribbon is received within the sheath, extends from the proximal end of the lead to the distal end of the lead, is fixed to the other end of the mounting member and defines a lumen through and in which a stylet can be received. A terminal pin/drive member at the proximal end of the lead has one end thereof connected to a proximal end of the ribbon and the other end thereof extending from the lead assembly. The terminal pin/drive member can be rotated to screw the securing device into living tissue and has a passageway therethrough opening into the lumen at one end and to the ambient environment at the other end.

19 Claims, 3 Drawing Figures

SCREW-IN PACING LEAD ASSEMBLY

BACKGROUND OF THE INVENTION

1. Field of the Invention

The present invention relates to pacing lead assemblies and more particularly to a screw-in pacing lead assembly having a corkscrew shaped securing device at the distal end thereof which is adapted to be threaded into living tissue for securing an electrode assembly at the distal end of the pacing lead to the living tissue such as to the endocardium in a ventricle or atrium of the heart.

2. Description of the Prior Art

Pacing lead assemblies have been in use for a number of years for supplying electrical stimulation pulses to or for receiving electrical pulses from living tissue. Such pacing lead assemblies have included a pacing lead comprising single or multiconductor coils of insulated wire having an insulating sheath thereabout with the lumen or cylindrical envelope defined by the coiled wire providing a space into which a stiffening stylet can be inserted. The conductive coil is connected to an electrode in an electrode assembly at the distal end of the pacing lead and typically a terminal member is mounted within a flexure sleeve at the proximal end of the pacing lead assembly and connected to the proximal end of the conductive coil.

A stylet is inserted into the pacing lead to provide stiffening of same when it is inserted into a vein for positioning the lead in living tissue such as in the endocardium in the ventricle or atrium of the heart or proximate thereto.

After the electrode assembly with an electrode at the tip thereof is positioned at a desired location within the heart it is desirable to provide some form of means for securing the electrode assembly at that location. One such means for securing the electrode assembly in place is a corkscrew (or helical) shaped securing device which is mounted at the distal end of the pacing lead assembly. Typically a proximal end of the corkscrew shaped securing device is fixed in a mounting member and the outer end thereof is adapted to be screwed into living tissue. In one such screw-in pacing lead assembly, a stylet with a specially configured distal end, such as a screwdriver shaped end, is adapted to be received in a mating slot in the rear end of the mounting member. Then the proximal end of the stylet is rotated within the pacing lead to cause the corkscrew shaped securing device to advance into living tissue.

This type of pacing lead assembly requires a stylet with a specially configured head. Also in this type of pacing lead assembly the stylet must be inserted all the way to the distal end of the pacing lead, properly located within a mating slot and then rotated to cause the corkscrew shaped securing device to be screwed into living tissue.

An example of such a screw-in pacing lead assembly is disclosed in U.S. Pat. No. 4,217,913 issued on Aug. 18, 1980 to Robert C. Dutcher and entitled BODY-IMPLANTABLE LEAD WITH PROTECTED EXTENDABLE TISSUE SECURING MEANS. Here the helix or corkscrew can be electrically insulated from the electrode or electrically coupled thereto as provided in an earlier screw-in-lead assembly disclosed in the Bisping U.S. Pat. No. 4,106,512.

Although such screw-in pacing lead assemblies have functioned adequately in the past, certain problems have been encountered with same. First of all, due to the non-linearity of a vein and the chambers of the heart, the stylet does a straight path to the mounting member at the distal end of the pacing lead. Rather it has a bowed or curved configuration within the lead. Accordingly, when the stylet is rotated, it tends to cause the pacing lead to move against the side wall of the vein or chamber of the heart in which it is located possibly causing trauma to the vessel or heart wall.

Also, the screwdriver shaped head at the distal end of the stylet has sharp edges which can damage the multiconductor coil in the lead as the stylet is moved through the coil. The head of the stylet also can catch on a turn of the coil and pierce through the insulating sheath.

Furthermore, such a screw-in pacing lead assembly requires that the distal end of the stylet be firmly located within a slot in the mounting member mounting the corkscrew shaped securing device. This is sometimes difficult to do and a physician manipulating the proximal end of the style is not always certain that he has effectively engaged the screwdriver shaped head of the stylet with the slot in the mounting member thereby to screw the corkscrew shaped securing device into living tissue.

It has also heretofore been proposed to provide a retaining coil at the end of an electrode system inserted into the vagina for monitoring fetal heartbeat in U.S. Pat. No. 3,827,428 issued to Edward H. Hon, et al. on Aug. 6, 1974 and entitled ELECTRODE STRUCTURE FOR MONITORING FETAL HEARTBEAT AND THE LIKE. In this electrode system for monitoring fetal heartbeat, a curved guide tube is adapted to be inserted through the vagina and cervix of a woman in labor. Then, a retaining coil mounted at the distal end of a holder mounted on the end of flexible driving tube within the guide tube can be rotated by rotating the driving tube to screw the retaining coil into living tissue. Two twisted leads are received within the flexible driving tube and extend from the retaining coil holder at the distal end thereof to the proximal end of the flexible driving tube received within the guide tube.

As will be described in greater detail hereinafter, the screw-in pacing lead assembly of the present invention provides a drive means receivable within a conventional pacing lead and fixed at the distal end thereof to a mounting member mounting a corkscrew shaped securing device and at its proximal end to a drive member. The drive mechanism defines a cylindrical envelope or lumen through which a stylet can be inserted for stiffening of the pacing lead when required but which stylet is not utilized in rotating the corkscrew shaped securing device into living tissue and which stylet can have a rounded distal end to facilitate insertion thereof into and through a pacing lead.

SUMMARY OF THE INVENTION

According to the invention, there is provided, a body-implantable lead assembly comprising a lead having a proximal end and a distal end, said proximal end being adapted to be connected to electrical means for supplying or receiving electrical pulses, said distal end being adapted to be connected to tissue of a living body, said lead comprising a sheath of material inert to body materials or fluids and at least one wire conductor having a proximal end and a distal end and extending from said proximal end of said lead within said sheath to said distal end of said lead, a terminal structure electrically coupled to said proximal end of said wire conductor and adapted to couple electrically said proximal end of said wire conductor to the electrical means, an electrode assembly including an electrode, said distal end of said wire conductor being electrically connected to said electrode, said electrode including a tubular body which has a proximal end and a distal end and said sheath being coupled to said proximal end of said tubular body, a corkscrew shaped securing device within said tubular body and having a proximal end and a distal end, a cylindrically shaped mounting member made of insulating material being received in said tubular body, flexible drive means being received within said sheath, having a proximal end and a distal end, extending from said proximal end of said lead to said distal end of said lead, said proximal end of said securing device being embedded in one end of said mounting member and said distal end of said drive means being embedded in the other end of said mounting member, with said ends of said drive means and said securing device being separated from each other within said mounting member, said flexible drive means being constructed to define a lumen or cylindrical envelope about the central area of said lead through and in which a stylet can be received, and a drive member at the proximal end of said lead fixed for rotation within said lead assembly, said drive member having one end thereof connected to the proximal end of said flexible drive means and the other end thereof extending from said lead assembly, said drive member further being adapted to be rotated to screw said securing device into living tissue and having a passageway therethrough opening into said lumen at one end and to the ambient environment at the other end and into which passageway a stylet can be inserted for passage through said drive means for stiffening said lead.

Further, according to the present invention, there is provided a body-implantable lead assembly comprising a lead having a proximal end and a distal end, said proximal end being adapted to be connected to electrical means for supplying or receiving electrical pulses, said distal end being adapted to be connected to tissue of a living body, said lead comprising a sheath of material inert to body materials or fluids and at least one wire conductor having a proximal end and a distal end and extending from said proximal end of said lead within said sheath to said distal end of said lead, a terminal structure electrically coupling to said proximal end of said wire conductor and adapted to couple electrically said proximal end of said wire conductor to the electrical means, an electrode assembly including an electrode, said distal end of said wire conductor being electrically connected to said electrode, said electrode including a tubular body which has a proximal end and a distal end and said sheath being coupled to said proximal end of said tubular body, a corkscrew shaped securing device within said tubular body and having a proximal end and a distal end, a mounting member received in said tubular body and having said proximal end of said securing device mounted on one end thereof, flexible drive means being received within and rotatable within said sheath, having a proximal end and a distal end, extending from said proximal end of said lead to said distal end of said lead and being fixed at its distal end to the other end of said mounting member in said tubular body, said flexible drive means being constructed to define a lumen or cylindrical envelope about the central area of said lead through and in which a stylet can be received, an elongate metal drive member at the proximal end of said lead and means for electrically coupling said wire conductor to said drive member, said drive member being fixed for rotation within said lead assembly, having one end thereof connected to the proximal end of said drive means and the other end thereof extending from said lead assembly and forming a proximal terminal pin of said terminal structure for coupling said lead assembly to the electrical means, said drive member further being adapted to be rotated to screw said securing device into living tissue and having a passageway therethrough opening into said lumen at one end and to the ambient environment at the other end and into which passageway a stylet can be inserted for passage through said drive means for stiffening said lead.

Still further, according to the present invention, there is provided a body-implantable lead assembly comprising a lead having a proximal end and a distal end, said proximal end being adapted to be connected to electrical means for supplying or receiving electrical pulses, said distal end being adapted to be connected to tissue of a living body, said lead comprising a sheath made of materials inert to body materials and fluids and at least one wire conductor having a proximal end and a distal end and extending from said proximal end of said lead within said sheath to said distal end of said lead, a terminal structure electrically said proximal end of said wire conductor and adapted to couple electrically said proximal end of said wire conductor to the electrical means, an electrode assembly including an electrode, said distal end of said wire conductor being electrically connected to said electrode, said electrode including a tubular body which has a proximal end and a distal end and said sheath being coupled to said proximal end of said tubular body, a corkscrew shaped securing device within said tubular body and having a proximal end and a distal end, a mounting member received in said tubular body and having said proximal end of said securing device mounted on one end thereof, flexible drive means defined by a generally flat, rectangular in cross-section helical ribbon fixed for rotation within said sheath, said helical ribbon having a proximal end and a distal end extending from said proximal end of said lead to said distal end of said lead, being fixed at its distal end to the other end of said mounting member in said tubular body and forming a non-removable part of said lead assembly, said helical ribbon defining a lumen or cylindrical envelope about the central area of said lead through and in which a stylet can be received, a drive member at the proximal end of said lead fixed for rotation within said lead assembly, said drive member having one end thereof connected to the proximal end of said helical ribbon drive means and the other end thereof extending from said lead assembly, said drive member further being adapted to be rotated to screw said securing device into living tissue and having a passageway therethrough opening into said lumen at one end and to the ambient environment at the other end and into which passageway a stylet can be inserted for passage through said drive means for stiffening said lead, and said helical ribbon drive means enabling one to rotate said corkscrew shaped securing device without twisting a curved distal end portion of said lead.

The drive means is preferably a helical metal ribbon fixed to the mounting member at the distal end thereof and to the drive member at the proximal end thereof. Also, the drive member is made of metal and serves a dual function as the terminal pin for the pacing lead assembly. Such drive means may also be rotated in a counterclockwise direction to retract the securing device from living tissue if the lead needs to be removed or repositioned.

DESCRIPTION OF THE PREFERRED EMBODIMENT

Figure 1:
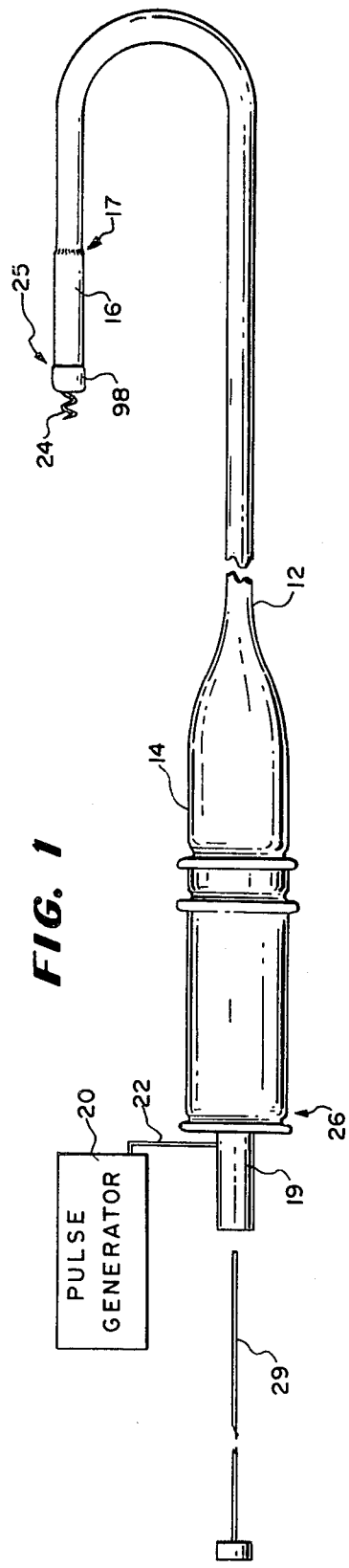
FIG. 1 is a plan view of the pacing lead assembly 10 of the present invention with portions of the pacing lead cut away and with the distal end of the stylet positioned to be inserted into the proximal end of the pacing lead assembly.

Referring now to the drawings in greater detail there is illustrated in FIG. 1 a screw-in pacing lead assembly 10 constructed in accordance with the teachings of the present invention and including a pacing lead 12, a flexure sleeve 14 at the proximal end 15 thereof and an electrode assembly 16 at the distal end 17 thereof. Inside the flexure sleeve 14 is a terminal housing 18 (FIG. 2) which is electrically connected in turn to a terminal pin/drive member 19 that is connected to a pulse generator 20 by an electrical connection shown schematically as a conductor 22 in FIG. 1.

Typically, in the field of pacing, the whole assembly 10 is referred to as the "pacing lead". However, in this description, the term "pacing lead assembly" is used since such assembly 10 includes not only the lead or lead body 12 but also the flexure sleeve 14 and the electrode assembly 16.

As will be described in greater detail in connection with the description of FIG. 3, the electrode assembly 16 includes a corkscrew shaped securing device 24 which extends from distal end 25 of the electrode assembly 16.

Extending from the proximal end 26 of the flexure sleeve 14 is terminal pin/drive member 19 which is constructed and operated in accordance with the teachings of the present invention for rotating the corkscrew device 24 into or out of living tissue after the electrode assembly 16 has been placed near living tissue such as adjacent the endocardium in a ventricle or atrium of the heart.

As will be described in greater detail hereinafter and in accordance with the teachings of the present invention, a stylet 29 can be inserted through the terminal pin/drive member 18 for positioning the electrode assembly 16 in a ventricle or atrium and/or for stiffening the pacing lead 12 before or after the pacing lead 12 with the electrode assembly 16 at the distal end thereof has been inserted into a body such as into a ventricle or atrium of the heart. Also, the stylet 29 is not used for rotating the corkscrew securing device 24 and is used only for stiffening the lead 12 and/or for positioning the electrode assembly 16 in a ventricle or atrium. If desired, a preformed or a preshaped "J" type stylet can be provided in the lead 12 for facilitating placement and attachment of the electrode assembly 16 in the atrium.

Figure 2:
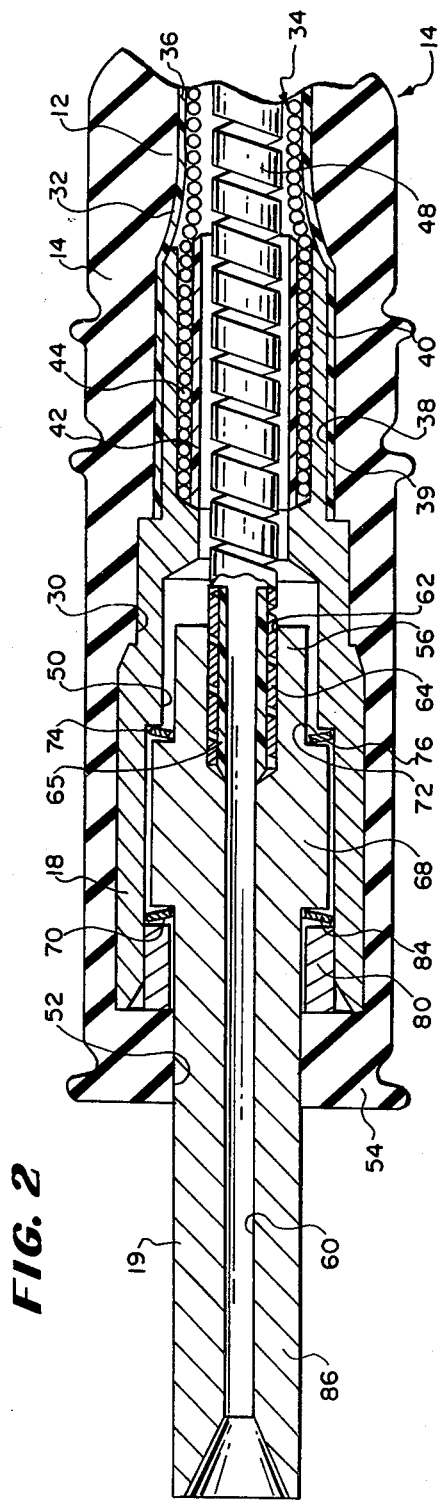
FIG. 2 is an enlarged sectional view of the flexure sleeve at the proximal end of the pacing lead assembly shown in FIG. 1.

Referring now to FIG. 2 the flexure sleeve 14 has an inner cylindrical cavity 30 machined therein in which is received the cylindrical terminal housing 18.

As shown, the lead 12 includes one or more filars or wire conductors 32 coiled in a coil 34 and surrounded by a sheath 36. The proximal end 15 of the lead 12 extends into the flexure sleeve 14 and through a cylindrical passageway 38 therein to the cylindrical cavity 30 where proximal end 39 of the sheath 36 is separated from the coil 34 and is received around a forward end portion 40 of the cylindrical terminal housing 18. A crimping sleeve 42 is received in the end portion 40 and a bare proximal end portion 44 of the conductor or filar 32 is coiled around the sleeve 42 and the end portion 40 crimped thereover.

To enhance the flexibility of the lead 12, the coil 34 consists of two or more coiled wire conductors 32 of small diameter connected in parallel between the ends thereof. Such parallel connection is effected by the respective coiling of the bare end of the conductors 32 about sleeve 42 at the proximal end thereof and about a sleeve (sleeve 108 in FIG. 3) at the distal ends thereof.

Figure 3:
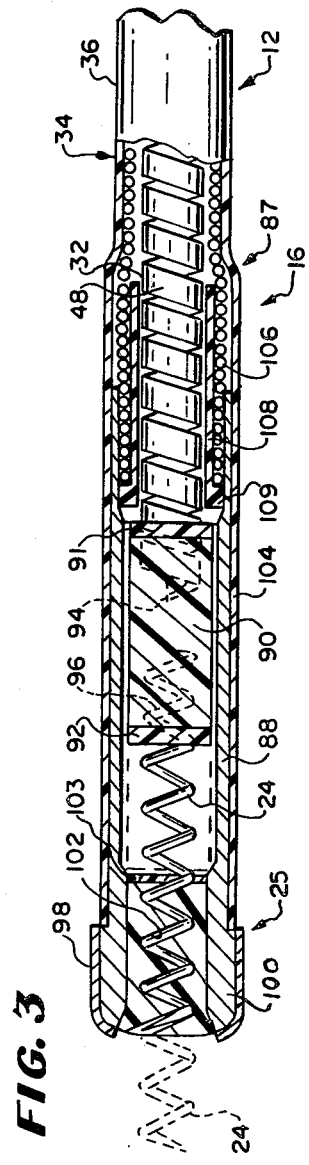
FIG. 3 is an enlarged sectional view of an electrode assembly at the distal end of the pacing lead assembly shown in FIG. 1.

In accordance with the teachings of the present invention and as shown in FIGS. 2 and 3, there is received within the lumen or cylindrical envelope defined within the coil 34 a drive mechanism 48 which is in the form of a flat helically wound metal ribbon 48. The helical ribbon 48 extends through the coil 34 of the lead 12 between a cavity 50 within the cylindrical terminal housing 18 and the electrode assembly 16.

Received within the cavity 50 of the cylindrical terminal housing 18 and through a cylindrical passageway 52 in an end wall 54 of the flexure sleeve 14 is a forward end portion 56 of the terminal pin/drive member 19. As shown, the terminal pin/drive member 19 is generally cylindrical in shape and has an axial passageway 60 therethrough opening at its forward end into the cavity 50 in the cylindrical terminal housing 18 and at its rearward end onto the ambient environment before it is inserted into a pulse generator 20. In the forward end portion 56 of the terminal pin/drive member 19 is a counterbore 62 which is larger than and coaxial with the axial passageway 60 and into which is received proximal end 64 of the helical flat metal ribbon 48. This proximal end 64 of the helical metal ribbon 48 is fixed within the counterbore 62 and around a sleeve 65.

Further, as shown in FIG. 2, the generally cylindrical terminal pin/drive member 19 has an annular boss 68 intermediate the ends thereof and closer to the forward end portion 56 thereof so as to be received within the cavity 50. The annular boss 68 has a rearward facing shoulder 70 and a forward facing shoulder 72. A metallic spring washer 74 is positioned between the forward facing shoulder 72 and a shoulder 76 formed in the cavity 50 within the cylindrical terminal housing 18 to provide electrical contact therebetween.

Between the inner surface of the end wall 64 of the flexure sleeve 54 and the annular boss 68 is positioned a metal ring 80. A second metallic spring washer 84 is positioned between the ring 80 and the rearward facing shoulder 70 on the annular boss 68. The washers 74 and 84 serve as thrust washers and/or bearing means for facilitating rotation of the terminal pin/drive member 19 and for establishing an electrical connection to the coil 34 from the terminal pin 19.

If desired, rear end portion 86 of the terminal pin/drive member 19 extending from the flexure sleeve 14 can be adapted for connection to a fixture to facilitate rotation of the terminal pin/drive member 19.

Referring now to FIG. 3 the drive mechanism consisting of the helically wound flat metal ribbon 48 extends to the electrode assembly 16 and is received in proximal end 87 of a metal tubular body 88 of the electrode assembly 16. Within the tubular body 88 is received a generally cylindrical non-conductive mounting member 90 having elastomeric (silastic) cushions 91 and 92 at the ends thereof. Distal end 94 of the helically wound flat metal ribbon 48 is secured within the proximal end of the mounting member 90 while proximal end 96 of the corkscrew shaped securing device 24 is received in the distal end of the mounting member 90.

The tubular body 88 has a smooth, porous-surfaced, annular cap-shaped electrode 98 which can be made of sintered metal and which is fixed to and integral with the distal end of tubular body 88. Fixed within the distal end of the tubular body 88 is a plug 100 having a helical or spiral passageway 102 therethrough through which the corkscrew securing device 24 is received. A sealing disc 103 made of silastic material is fixed to the inner end of plug 100 for preventing intrusion of body fluids into the tubular body 88.

As shown, a distal end 104 of the sheath 36 extends over the metal tubular body 88 and to the annular cap-shaped electrode 98 thereof. A bare end portion 106 of the coiled wire conductor(s) 32 is coiled about a sleeve 108 received within proximal end 87 of the tubular body 88 such that the outer surface of the coil is in intimate contact with the interior surface of the distal end of the metal tubular body 88 and in good electrical contact therewith. The sleeve 108 has a shoulder at the distal end 109 thereof which limits inward movement of the bared coiled wire conductor end portion 105 and which serves as a backstop for block 90, namely for the silastic cushion 91. As shown, the helical metal ribbon 48 is received through the insulating sleeve 108 for mounting in the mounting member 90.

It will be appreciated from the foregoing description that the terminal pin/drive member 19 can be rotated to cause rotation of the helical metal ribbon 48 which in turn rotates the mounting member 90. Such rotation of the mounting member 90 causes the corkscrew shaped securing device 24 to be rotated or threaded within the spiral or helical passageway 102 in the plug 100 which acts as a nut thereby causing the corkscrew shaped securing device 24 to be moved axially in or out of the tubular body 88 or the electrode assembly 16.

In this way, the corkscrew shaped securing device 24 can be screwed into living tissue to anchor the electrode assembly 16 in the living tissue such as the endocardium in the ventricle or atrium of a heart.

Also it will be appreciated from the foregoing description that the lumen or cylindrical envelope defined by and within the helically wound metal ribbon 48 enables a stylet 29 to be inserted within the lead 12 and more particularly within the lumen or cylindrical envelope of the helically wound metal ribbon 48 for stiffening the lead 12 when it is inserted into a body, such as into a vein, and/or for positioning the electrode assembly 16 in the ventricle or atrium.

Also it will be appreciated that the stylet 29 is not needed for rotating the corkscrew shaped securing device 24 into living tissue and can have a rounded tip. Further it will be appreciated that the terminal pin/drive member 19 can be rotated with or without a stylet 29 passing therethrough into the lead 12.

Thus, the construction of the screw-in pacing lead assembly 10 of the present invention described above provides a simple means for rotating the corkscrew shaped securing device 24 into or out of living tissue and with or without a stylet 29 received in the lead 12. With this construction, the distal end of the stylet 29 need not be configured with a special drive configuration such as a screwdriver head for being received in a mating head in the end of a mounting member such as mounting member 90. This enables the use of a rounded distal end stylet 29 which minimizes catching of the end of the stylet 29 on turns of the coil 34 and/or piercing through the sheath 26 of the lead 12.

Moreover, with the fixed connections between the proximal end 64 of the helically wound metal ribbon 48 to the drive member 19 and the distal end thereof to the mounting member 90, a physician rotating the terminal pin/drive member 19 can be certain that the corkscrew shaped securing device 24 is being moved into or out of living tissue.

This is particularly important when such drive mechanism 48 is used in a J-atrial pacing lead, with or without a stylet therein. In this respect, rotation of the drive mechanism, namely ribbon 48, is achieved notwithstanding the U-shaped bight of the J shaped distal end and without twisting or bowing out of the lead 12. Then the stylet 29 can be used for stiffening and/or positioning the electrode assembly 16 in an atrium.

From the foregoing description it will be appreciated that the screw-in pacing lead assembly 10 of the present invention has a number of advantages, some of which have been described above and others of which are inherent in the invention. Also it will be apparent to those skilled in the art that modifications can be made to the screw-in pacing lead assembly 10 of the present invention without departing from the teachings of the present invention. For example, with the mounting member 90 and plug 100 being made of insulating material, the corkscrew shaped securing device 24 is insulated from the electrode 98. Also, this construction, with the mounting member 90 and plug 100 being made of insulating materials, facilitates use of the screw-in pacing lead assembly 10 with bipolar or multielectrode assemblies in place of the unipolar electrode assembly 16. Accordingly, the scope of the invention is only to be limited as necessitated by the accompanying claims.

I claim:

1. A body-implantable lead assembly comprising a lead having a proximal end and a distal end, said proximal end being adapted to be connected to electrical means for supplying or receiving electrical pulses, said distal end being adapted to be connected to tissue of a living body, said lead comprising a sheath of material inert to body materials or fluids and at least one wire conductor having a proximal end and a distal end and extending from said proximal end of said lead within said sheath to said distal end of said lead, a terminal structure electrically coupled to said proximal end of said wire conductor and adapted to couple electrically said proximal end of said wire conductor to the electrical means, an electrode assembly including an electrode, said distal end of said wire conductor being electrically connected to said electrode, said electrode including a tubular body which has a proximal end and a distal end and said sheath being coupled to said proximal end of said tubular body, a corkscrew shaped securing device within said tubular body and having a proximal end and a distal end, a cylindrically shaped mounting member made of insulating material being received in said tubular body, flexible drive means being received within and rotatable within said sheath, having a proximal end and a distal end and extending from said proximal end of said securing device being embedded in one end of said mounting member and said distal end of said drive means being embedded in the other end of said mounting member, with said ends of said drive means and said securing device being separated from each other within said mounting member, said flexible drive means being constructed to define a lumen or cylindrical envelope about the central area of said lead through and in which a stylet can be received, and a drive member at the proximal end of said lead fixed for rotation within said lead assembly, said drive member having one end thereof connected to the proximal end of said flexible drive means and the other end thereof extending from said lead assembly, said drive member further being adapted to be rotated to screw said securing device into living tissue and having a passageway therethrough opening into said lume at one end and to the ambient environment at the other end and into which passageway a stylet can be inserted for passage through said drive means for stiffening said lead.

2. The lead assembly of claim 1 wherein said drive means are defined by a helical ribbon having a proximal end and a distal end and being fixed to said mounting member at said distal end thereof and to said drive member at said proximal end thereof.

3. The lead assembly of claim 2 wherein said helical ribbon is made of metal.

4. The lead assembly of claim 2 wherein said at least one wire conductor is coiled within said sheath and said conductor extends the length of said lead in a coil with said helical ribbon extending through said coil.

5. The lead assembly of claim 4 wherein said coil comprises two or more coiled wire conductors of small diameter connected in parallel between the ends of said lead to enhance the flexibility of said lead.

6. The lead assembly of claim 1 wherein said mounting member has an elastomeric cushion at each end thereof for cushioning engagement thereof with parts of said electrode assembly in said tubular body when said mounting member is moved axially by said drive means.

7. The lead assembly of claim 1 including a plug fixed in said tubular body adjacent the distal end thereof, said plug being made of an insulating material and having a helical passageway therein through which said corkscrew device is received such that rotation of said corkscrew device by said drive means causes said corkscrew device to move axially of said plug in and out of said tubular body through said helical passageway in said plug.

8. The lead assembly of claim 7 wherein said plug has a silastic sealing disc on the inner end of said plug for preventing intrusion of body fluids into said electrode assembly.

9. The lead assembly of claim 1 wherein said tubular body is made of metal.

10. The lead assembly of claim 9 wherein said sheath extends about said tubular body, said corkscrew device extends through a plug adjacent the distal end of said tubular body and said electrode is defined by a smooth, porous-surfaced, generally annular shaped cap formation at and integral with the distal end of said tubular body.

11. The lead assembly of claim 9 including an insulating sleeve positioned within the proximal end of said tubular body and having said drive means passing therethrough, a bare proximal end of the at least one wire conductor being coiled about the outer surface of said sleeve and in electrical contact with the inner surface of said metal tubular body at the proximal end thereof.

12. The lead assembly of claim 11 wherein said sleeve has a distal end and has a shoulder at the distal end thereof to limit forward movement of said bare coiled wire conductor and to form a backstop for said mounting member.

13. A body-implantable lead assembly comprising a lead having a proximal end and a distal end, said proximal end being adapted to be connected to electrical means for supplying or receiving electrical pulses, said distal end being adapted to be connected to tissue of a living body, said lead comprising a sheath of material inert to body materials or fluids and at least one wire conductor having a proximal end and a distal end and extending from said proximal end of said lead within said sheath to said distal end of said lead, a terminal structure electrically coupled to said proximal end of said wire conductor and adapted to couple electrically said proximal end of said wire conductor to the electrical means, an electrode assembly including an electrode, said distal end of said wire conductor being electrically connected to said electrode, said electrode including a tubular body which has a proximal end and a distal end and said sheath being coupled to said proximal end of said tubular body, a corkscrew shaped securing device within said tubular body and having a proximal end and a distal end, a mounting member received in said tubular body and having said proximal end of said securing device mounted on one end thereof, flexible drive means being received within and rotatable within said sheath, having a proximal end and a distal end, extending from said proximal end of said lead to said distal end of said lead and being fixed at its distal end to the other end of said mounting member in said tubular body, said flexible drive means being constructed to define a lumen or cylindrical envelope about the central area of said lead through and in which a stylet can be received, an elongate metal drive member at the proximal end of said lead and means for electrically coupling said conductor to said drive member, said drive member being fixed for rotation within said lead assembly, having one end thereof connected to the proximal end of said drive means and the other end thereof extending from said lead assembly and forming a proximal terminal pin of said terminal structure for coupling said lead assembly to the electrical means, said drive member further being adapted to be rotated to screw said securing device into living tissue and having a passageway therethrough opening into said lumen at one end and to the ambient environment at the other end and into which passageway a stylet can be inserted for passage through said drive means for stiffening said lead.

14. The lead assembly of claim 13 including a flexure sleeve at the proximal end of said lead, the proximal end of said lead extending into said flexure sleeve and said terminal pin/drive member being mounted for rotation within said flexure sleeve.

15. The lead assembly of claim 16 wherein said flexure sleeve has a generally cylindrical cavity therein and wherein said terminal structure includes a generally cylindrical terminal housing mounted within said cavity and having a forward end portion about which the proximal end of said sheath is received, a sleeve received in said forward end portion and a bare proximal end portion of said wire conductor received in and coiled about said sleeve and between the outer surface of said sleeve and the inner surface of the forward end portion of said cylindrical terminal housing which is crimped over said coiled bare wire end portion and said sleeve, said terminal pin/drive member being received within said flexure sleeve and within said terminal housing and having said drive means fixed thereto.

16. The lead assembly of claim 15 wherein said terminal pin/drive member has a counterbore at its forward end and wherein said drive means comprise a helical metal ribbon having its proximal end secured in said counterbore about a sleeve.

17. The lead assembly of claim 15 wherein said terminal pin/drive member is generally cylindrical in shape, has an annular boss extending therearound intermediate the ends thereof and is received within said flexure sleeve and the rearward end of said cylindrical terminal housing, wherein a metal ring is positioned around the rearward end of said terminal pin/drive member and within said terminal housing between an end wall of said flexure sleeve and one shoulder of said annular boss and wherein said terminal housing has an annular shoulder therein in front of said annular boss for limiting axial movement of said drive member.

18. The lead assembly of claim 17 including a first metal spring washer between said ring and said one shoulder of said annular boss and a second metal spring washer between the other shoulder of said annular boss and said shoulder in said cylindrical terminal member, said metal spring washers providing an electrical connection between said terminal housing and said terminal pin/drive member as well as providing a thrust bearing function.

19. A body-implantable lead assembly comprising a lead having a proximal end and a distal end, said proximal end being adapted to be connected to electrical means for supplying or receiving electrical pulses, said distal end being adapted to be connected to tissue of a living body, said lead comprising a sheath made of materials inert to body materials and fluids and at least one wire conductor having a proximal end and a distal end and extending from said proximal end of said lead within said sheath to said distal end of said lead, a terminal structure electrically coupled to said proximal end of said wire conductor and adapted to couple electrically said proximal end of said wire conductor to the electrical means, an electrode assembly including an electrode, said distal end of said wire conductor being electrically connected to said electrode, said electrode including a tubular body which has a proximal end and a distal end and said sheath being coupled to said proximal end of said tubular body, a corkscrew shaped securing device within said tubular body and having a proximal end and a distal end, a mounting member received in said tubular body and having said proximal end of said securing device mounted on one end thereof, flexible drive means defined by a generally flat, rectangular in cross-section helical ribbon fixed for rotation within said sheath, said helical ribbon having a proximal end and a distal end, extending from said proximal end of said lead to said distal end of said lead, being fixed at its distal end to the other end of said mounting member in said tubular body and forming a non-removable part of said lead assembly, said helical ribbon defining a lumen or cylindrical envelope about the central area of said lead through and in which a stylet can be received, a drive member at the proximal end of said lead fixed for rotation within said lead assembly, said drive member having one end thereof connected to the proximal end of said helical ribbon drive means and the other end thereof extending from said lead assembly, said drive member further being adapted to be rotated to screw said securing device into living tissue and having a passageway therethrough opening into said lumen at one end and to the ambient environment at the other end and into which passageway a stylet can be inserted for passage through said drive means for stiffening said lead, and said helical ribbon drive means enabling one to rotate said corkscrew shaped securing device without twisting a curbed distal end portion of said lead.

* * * * *

UNITED STATES PATENT AND TRADEMARK OFFICE
CERTIFICATE OF CORRECTION

PATENT NO. : 4,463,765
DATED : August 7, 1984
INVENTOR(S) : Philip Gold

It is certified that error appears in the above-identified patent and that said Letters Patent is hereby corrected as shown below:

Column 2, line 36 after "of" there should be inserted --a--.

Column 3, line 13, after "within" there should be inserted --and rotatable within--.

Column 3, line 48 "coupling" should have been --coupled--.

Column 4, line 28, after "electrically" there should be insert --coupled to--.

Column 5, line 56 "18" should have been --19--.

Column 7, line 35 "105" should have been --106--

Column 7, line 49 "or" should have been --of--.

Column 10, line 7 "the" should have been --said--.

Column 10, line 63 "16" should have been --14--.

Signed and Sealed this

Twentieth Day of August 1985

[SEAL]

Attest:

DONALD J. QUIGG

Attesting Officer        Acting Commissioner of Patents and Trademarks